United States Patent [19]

Gassen et al.

[11] Patent Number: 5,124,476
[45] Date of Patent: Jun. 23, 1992

[54] PROCESS FOR THE PREPARATION OF α-FLUOROACRYLOYL DERIVATIVES

[75] Inventors: Karl-Rudolf Gassen, Odenthal; Albrecht Marhold, Leverkusen, both of Fed. Rep. of Germany

[73] Assignee: Bayer Aktiengesellschaft, Leverkusen, Fed. Rep. of Germany

[21] Appl. No.: 566,590

[22] Filed: Aug. 13, 1990

[30] Foreign Application Priority Data

Sep. 1, 1989 [DE] Fed. Rep. of Germany ....... 3928990

[51] Int. Cl.$^5$ .............................................. C07C 67/30
[52] U.S. Cl. .................... 560/213; 560/219; 562/526; 568/946
[58] Field of Search ........................ 568/946; 562/526; 560/213, 219

[56] References Cited

U.S. PATENT DOCUMENTS 152,235  6/1867  Knunyants et al. ................. 562/526
4,533,776  8/1985  Baasner et al. ....................... 568/946
4,604,482  8/1986  Ohmori et al. ....................... 560/213

OTHER PUBLICATIONS

E. Earl Royals, *Advanced Organic Chemistry* ©1984 by Prentice-Hall, Inc. fourth printing, May 1959, p. 600.

*Primary Examiner*—Bruce Gray
*Assistant Examiner*—Keith MacMillan
*Attorney, Agent, or Firm*—Sprung, Horn, Kramer & Woods

[57] ABSTRACT

α-Fluoroacryloyl derivatives are prepared by reacting a dihalogenopropene with an anhydrous mixture of nitric acid and hydrofluoric acid to give a 1-nitro-2,2-fluorohalogeno-3-halogenopropane, converting this in the presence of a strong acid and a little water at elevated temperature to a 2,2-fluorohalogeno-3-halogenopropanoic acid, converting this into an ester or an amide and finally treating this with a dehalogenating agent.

7 Claims, No Drawings

PROCESS FOR THE PREPARATION OF α-FLUOROACRYLOYL DERIVATIVES

The present invention relates to an advantageous process for the preparation of α-fluoroacryloyl derivatives starting from dihalogenopropenes.

Derivatives of α-fluoroacrylic acid are versatile organic intermediates and can, in particular be used as monomers for the preparation of polymers for optical glasses, optical fibres and the sheathings thereof (cf., for example, EP-A 0,128,517). The hitherto known processes for the preparation of α-fluoroacryloyl derivatives have the disadvantages that they require many reaction steps, give poor yields, require toxic chemicals which are difficult to obtain and are consequently costly and whose handling requires particular safety precautions, are not reproducible and/or only allow the preparation of small quantities.

For instance, it was hitherto known to prepare 2-fluoroacryloyl fluoride from tetrafluorohydroxyethane (cf. EP-A-0,148,490) which is only accessible with great technical effort and is very toxic. The synthesis starting from fluoroacetic acid has the same disadvantages (cf. US-A-3,075,002). A process starting from 1,2-dibromo-3-chloropropane requires many reaction steps (cf. Zh. Org. Khim 28 1173 (1987)). An electrochemical method of preparation (cf. DE-A-3,704,915) requires highly complex apparatus and does not always give reproducible results.

There is therefore a need for an effective and easy-to-use process for the preparation of α-fluoroacryloyl derivatives on an industrial scale.

A process for the preparation of α-fluoroacryloyl derivatives has now been found which is characterized in that a) a dihalogenopropene of the formula (I)

$$CH_2=CHal^1-CH_2Hal^2 \qquad (I),$$

in which
Hal$^1$ and Hal$^2$, independently of one another, represent chlorine or bromine, is reacted with an anhydrous mixture of nitric acid and hydrofluoric acid to give a 1-nitro-2,2-fluorohalogeno-3-halogenopropane of the formula (II)

$$CH_2Hal^2-CFHal^1-CH_2NO_2 \qquad (II),$$

in which
Hal$^1$ and Hal$^2$ have the meaning given in formula (I), b) converting this in the presence of a strong acid and a little water at elevated temperature to a 2,2-fluorohalogeno-3-halogenopropanoic acid of the formula (III)

$$CH_2Hal^2-CFHal^1-COOH \qquad (III),$$

in which
Hal$^1$ and Hal$^2$ have the meaning given in formula (I), c) converting this into a derivative of the formula (IV)

$$CH_2Hal^2-CFHal^1-CO-R \qquad (IV),$$

in which
Hal$^1$ and Hal$^2$ have the meaning given in formula (I) and R represents OR$^1$ where R$^1$ = optionally substituted, straight chain, branched or cyclic C$_1$-C$_{18}$-alkyl, optionally substituted C$_6$-C$_{14}$-aryl or C$_6$-C$_{14}$-heteroaryl or represents NR$^2$R$^3$ where R$^2$ and R$^3$, independently of one another, optionally substituted, straight chain, branched or cyclic C$_1$-C$_{18}$-alkyl or where R$^2$ and R$^3$ form a 5- to 7-membered ring together with the nitrogen atom which is located between them and d) this is reacted with a dehalogenating agent to give an α-fluoroacryloyl derivative of the formula (V)

$$CH_2=CF-CO-R \qquad (V),$$

in which
R has the meaning given in formula (IV).

In the formulae (I) to (IV), Hal$^1$ and Hal$^2$ preferably represent chlorine. Insofar as the radicals R$^1$, R$^2$ and R$^3$ can be substituted, the substituents are preferably halogen atoms, in particular fluorine atoms.

The reaction of the dihalogenopropene of the formula (I) with an anhydrous mixture of nitric acid and hydrofluoric acid can be carried out, for example, at temperatures in the range of from $-50°$ to $+30°$ C. Preference is given to temperatures of $-10°$ to $+20°$ C.

The anhydrous mixture of nitric acid and hydrofluoric acid can be obtained by mixing the anhydrous components, but also, for example, by adding sulphur trioxide or chlorosulphonic acid to hydrous mixtures of nitric acid and hydrofluoric acid.

Relative to 1 mol of dihalogenopropene of the formula (I) it is possible to use nitric acid, for example, in amounts from 0.9 to 10 mol and hydrofluoric acid, for example, in amounts from 2 to 50 mol. Preference is given to the use, per mol of dihalogenopropene of the formula (I), of 1 to 2 mol of nitric acid and 5 to 30 mol of hydrofluoric acid.

The reaction of the dihalogenopropene of the formula (I) with the nitric acid/hydrofluoric acid mixture can be carried out, for example, by first charging the acid mixture, then slowly adding the dihalogenopropene and stirring for some time after the addition has ceased. The reaction mixture can be worked up, for example, by distilling off the excess hydrofluoric acid in vacuo for example and thus recovering it and using the residue without further post-treatment, optionally in the same reaction vessel, for the next reaction step. The residue may also be poured on to ice, washed with water and, after phase separation, the organic phase, which still contains some water, can be used in the next reaction step. The organic phase may optionally be treated with a drying agent, for example sodium sulphate or calcium chloride.

If desired, the solution which has been purified and dried in this manner can be freed from solvent by evaporation and distilled in vacuo to give pure 1-nitro-2,2-fluorohalogeno-3-halogenopropane of the formula (II). Isolation of the product in this manner may require special safety measures since spontaneous decompositions can occur.

The conversion to the corresponding 2,2-fluorohalogeno-3-halogenopropanoic acid of the formula (III) requires a strong-acid catalysis. Suitable strong acids are in particular sulphuric acid, phosphoric acid, nitric acid, hydrochloric acid and hydrobromic acid. Preference is given to sulphuric acid. If the strong acid is volatile at the temperatures which are to be used, it is necessary to operate in closed vessels under pressure. The strong acid may, for example, be used in amounts of 1 to 100 mol per mol of the compound of the formula (II). This amount preferably is from 3 to 50 mol.

The conversion is carried out in the presence of a little water, for example 0.9 to 20 mol of water per mol of compound of the formula (II). This amount is preferably 1 to 10 mol, particularly preferably 3 to 8 mol. The water may be introduced into the reaction mixture in various ways, for example in the form of a hydrous, preferably in excess of 90% strength by weight acid and/or in the form of a hydrous compound of the formula (II).

The water which is required may be added as such to the reaction mixture. It should be noted that the amounts of water given above relate to the sum of the overall amount of water which is present in the reaction mixture at the start of the reaction and that normally no more water is added during the reaction.

The conversion may, for example, be carried out at temperatures in the range of from 50° to 200° C. Preferably the reaction mixture is heated slowly or in steps and the reaction is brought to completion, for example, in the course of 1 to 20 hours at 50° to 150° C.

The 2,2-fluorohalogeno-3-halogenocarboxylic acid of the formula (III) which has been obtained in this manner can be isolated, for example, from the reaction mixture by adding the mixture to ice and then extracting the mixture one or more times with one or more inert, water-immiscible solvents, drying the combined organic phases, evaporating off the solvent(s) and distilling the remaining residue, preferably in vacuo.

The subsequent formation of derivatives to give compounds of the formula (IV) can be carried out in a manner known per se. Compounds of the formula (IV) in which $R=OR^1$ can be obtained by esterification of an acid of the formula (III) with the corresponding alcohol $HOR^1$.

The preparation of compounds of the formula (IV) in which $R=NR^2R^3$ requires that the acid of the formula (III) is first converted into the corresponding acid chloride, for example using thionyl chloride. The acid chloride can then be reacted with an amine of the formula $HNR^2R^3$ to give the amide of the formula (IV) in which $R=NR^2R^3$.

The preparation of esters of the formula (IV) in which $R=OR^1$ can also be carried out by first converting the acid of the formula (III) into the corresponding acid chloride and then esterifying this with an alcohol $HOR^1$. This method is preferably selected if the alcohol $HOR^1$ is not stable in the acid medium, but has, for example, a tendency to undergo rearrangements.

In the formulae (IV) and (V), R preferably represents $C_1$-$C_{18}$-alkoxy or -fluoroalkoxy or an amido group $NR^2R^3$ in which $R^2=R^3$ and each of these is a $C_1$-$C_{18}$-alkyl or -fluoroalkyl radical, or represents an amido group $NR^2R^3$ in which $R^2$ and $R^3$ form a 5- to 7-membered ring together with the nitrogen atom which is located between them.

Suitable dehalogenating agents for converting a compound of the formula (IV) into a compound of the formula (V) are for example zinc, magnesium or chromium (II) chloride in the presence of protic or aprotic solvents. The dehalogenation can also be carried out electrochemically. Preference is given to zinc in the presence of water or diglyme. Examples of suitable temperatures for the dehalogenation are those from 0° to 150° C.

The product can be worked up by distilling off from the reaction mixture the α-fluoroacryloyl derivative of the formula (V) which has been formed, optionally together with water, separating off and drying the organic components of the distillate and purifying the product by a further distillation.

The present invention provides the preparation of α-fluoroacryloyl derivatives in a simple manner in few reaction steps, with good yields, by the use of inexpensive, readily accessible chemicals and in customary apparatuses. The invention is therefore particularly suitable for the preparation of α-fluoroacryloyl derivatives on an industrial scale.

It is particularly surprising that the process according to the invention can be carried out so simply and effectively, because hitherto it was known only that 1-nitro-2,2-fluorohalogeno-3-halogenopropane can be prepared at temperatures from −30° to −40° C. in liquid sulphur dioxide using $NO_2BF_4$ (cf. I zv. Akad. Nauk SSSR, Ser. Khim., No. 3, pp. 654–657, Mar. 1982). $NO_2BF_4$ is a costly reagent which is difficult to prepare and is only available in small amounts and the mode of operation in liquid sulphur dioxide is extremely expensive as an industrial process.

Since these surprising effects occur in particular in the first step of the process according to the invention for the preparation of α-fluoroacryloyl derivatives of the formula (V), the present invention also provides a process for the preparation of 1-nitro-2,2-fluorohalogeno-3-halogenopropane of the formula (II)

$$CH_2Hal^2-CFHal^1-CH_2NO_2 \quad (II)$$

in which $Hal^1$ and $Hal^2$, independently of one another, represent chlorine or bromine, which is characterized in that a dihalogenopropene of the formula (I)

$$CH_2=CHal^1-CH_2Hal^2 \quad (I)$$

in which $Hal^1$ and $Hal^2$ have the meaning given in formula (II), is reacted with an anhydrous mixture of nitric acid and hydrofluoric acid.

EXAMPLES

Example 1

Preparation of 2,3-dichloro-2-fluoro-1-nitropropane

To a mixture of 86 ml of anhydrous, 100% strength nitric acid and 300 ml of anhydrous hydrofluoric acid were added dropwise at −10° C. in the course of 3 hours 111 g (1 mol) of 2,3-dichloropropene. The reaction was slightly exothermic. After the dropwise addition had ceased, stirring was continued for a further 1 hour at −10° C. Then the mixture was poured on to ice and extracted using dichloromethane. The organic phase was washed with sodium hydrogencarbonate solution, dried over sodium sulphate and concentrated using a rotary evaporator. The crude product was distilled under an oil pump vacuum. This gave 115.8 g (=63% of theory) of product having a boiling point of 48° to 50° C. at 0.07 mbar and a Refractive Index $n_D^{20}$ of 1.4578 (at 24° C.). The product was 95.7% pure.

Since there is a risk of the distillation mixture decomposing, further preparations of 2,3-dichloro-2-fluoro-1-nitropropane were carried out in accordance with Example 2.

EXAMPLE 2

Preparation of 2,3-dichloro-2-fluoro-1-nitropropane

To a mixture of 970 ml of anhydrous, 100% strength nitric acid and 3380 ml of anhydrous hydrofluoric acid were added dropwise at −10° C. in the course of 5 hours 1250 g (11.3 mol) of 2,3-dichloropropene. The reaction was exothermic. After the dropwise addition had ceased, the mixture was poured on to ice. The organic phase was separated off and washed with a large quantity of water. This gave 1316 g of moist product (=66% of theory) having a purity of 97%. The water content of the product was 0.5%.

EXAMPLE 3

Preparation of 2,3-dichloro-2-fluoropropanoic acid

A mixture of 1170 g (6.65 mol) of 2,3-dichloro-2-fluoro-1-nitropropane (97% pure), 1500 ml of concentrated sulphuric acid and 10 ml of water was slowly heated and stirred for 2 hours at 80° C., 4 hours at 100° C. and 6 hours at 120° C. The batch was poured on to ice, extracted first with chloroform and then with diethyl ether, the organic phases were combined and then these were dried over sodium sulphate. Then the solvent was evaporated off using a rotary evaporator and the residue was distilled under water pump vacuum. This gave 925 g (=87% of theory) of product having a boiling point at 18 mbar of 98° to 101° C. The purity of the product was 92%. On cooling the receiver, the product solidified.

EXAMPLE 4

Preparation of 2,3-dichloro-2-fluoropropanoic acid chloride.

A mixture of 1096.5 g (6.8 mol) of 2,3-dichloro-2-fluoropropanoic acid (92% strength) and 2052 g (17.3 mol) of thionyl chloride was slowly heated and stirred at 78 to 80° C. until gas evolution had ceased. After 16 hours gas chromatographic analysis showed that conversion was complete. The excess thionyl chloride was then distilled off over a 60 cm packed column, followed by the product. This gave 665 g (=60% of theory) of product having a boiling point of 54° C. at 50 mbar. The purity of the product was 99.3%.

EXAMPLE 5

Preparation of the n-butyl ester of 2,3-dichloro-2-fluoropropanoic acid.

To a mixture of 159 g (2.15 mol) of n-butanol and 217 g (2.15 mol) of triethylamine in 1200 ml of anhydrous diethyl ether were added dropwise at 15° to 20° C. 350 g (1.95 mol) of 2,3-dichloro-2-fluoropropanoic acid chloride and then stirring was continued for a further 2 hours at room temperature. The mixture was then cooled to 0° C. and the precipitated solid was filtered off under suction and washed well with diethyl ether. The organic phases were combined, washed once with dilute hydrochloric acid, dried over sodium sulphate, concentrated using a rotary evaporator and then distilled. This gave 360 g (=83% of theory) of product having a boiling point of 99° to 101° C. at 26 mbar. The product had a purity of 97%.

EXAMPLE 6

Preparation of n-butyl α-fluoroacrylates

To a mixture of 340 g of zinc which had been freshly activated using 5% strength $H_2SO_4$, 700 ml of water and 1 ml of concentrated sulphuric acid were added dropwise at 110° C. 338 g (1.56 mol) of n-butyl ester of 2,3-dichloro-2-fluoropropanoic acid. The product distilled off as an azeotrope. The organic phase of the distillate was separated off and the aqueous phase extracted thoroughly with diethyl ether. The separated organic phase and the diethyl ether phases were combined, dried, concentrated using a rotary evaporator and then distilled. This yielded 146.6 g (=73% of theory) of product having a boiling point of 49° to 51° C. at 24 mbar. The purity of the product was 98%.

What is claimed is:

1. A process for the preparation of a α-fluoroacryloyl derivatives, in which
   a) a dihalogenopropene of the formula (I)

$$CH_2=CHal^1-CH_2Hal^2 \qquad (I),$$

in which $Hal^1$ and $Hal^2$, independently of one another, represent chlorine or bromine, is reacted with an anhydrous mixture of nitric acid and hydrofluoric acid to give a 1-nitro-2,2-fluorohalogeno-3-halogenopropane of the formula (II)

$$CH_2Hal^2-CFHal^1-CH_2NO_2 \qquad (II).$$

in which $Hal^1$ and $Hal^2$ have the meaning given in formula (I), b) converting this in the presence of a strong acid selected from the group consisting of sulphuric acid, phosphoric acid, nitric acid, hydrochloric acid, and hydrobromic acid, and 0.9 to 20 mol of water per mol of compound of the formula (II) at elevated temperature in the range of from 50° to 200° C. to a 2,2-fluorohalogeno-3-halogenopropanic acid of the formula $$CH_2Hal^2-CFHal^1-COOH \qquad (III),$$

in which $Hal^1$ and $Hal^2$ have the meaning given in formula (I), c) converting this into a derivative of the formula (IV)

$$CH_2Hal^2-CFHal^1-CO-R \qquad (IV),$$

in which $Hal^1$ and $Hal^2$ have the meaning given in formula (I) and
R represents $OR^1$ where $R^1$=optionally substituted, straight chain, branched or cyclic $C_1$-$C_{18}$-alkyl, optionally substituted $C_6$-$C_{14}$-aryl or $c_6$-$C_{14}$-heteroaryl or represents $NR^2R^3$ where $R^2$ and $R^3$, independently of one another, represent optionally substituted, straight chain, branched or cyclic $C_1$-$C_{18}$-alkyl or where $R^2$ and $R^3$ form a 5- to 7-membered ring together with the nitrogen atom which is located between them and d) this is reacted with a dehalogenating agent to give an α-fluoroacryloyl derivative of the formula (V)

$$CH_2=CF-CO-R \qquad (V),$$

in which
R has the meaning given in formula (IV).

2. The process of claim 1, in which in the formulae (I) to (IV), $Hal^1$ and $Hal^2$ represent chlorine.

3. The process of claim 1, in which step a) is carried out at temperatures in the range of from −50° to +30° C.

4. The process of claim 1, in which in step a) 0.9 to 10 mol of nitric acid and 2 to 50 mol of hydrofluoric acid are used, relative in each case to 1 mol of dihalogenopropene of the formula (I).

5. The process of claim 1, in which step b) is carried out in the presence of 1 to 100 mol of a strong acid per mol of the compound of the formula (II).

6. The process of claim 1, in which step b) is carried out in the presence of 0.9 to 20 mol of water per mol of the compound of the formula (II).

7. The process of claim 1, in which step b) is carried out at temperatures in the range of from 50° to 200° C.

* * * * *